United States Patent
Liao et al.

(10) Patent No.: US 9,058,664 B2
(45) Date of Patent: Jun. 16, 2015

(54) 2D-2D FUSION FOR INTERVENTIONAL GUIDANCE IN TRANS-CATHETER AORTIC VALVE IMPLANTATION

(75) Inventors: Rui Liao, Princeton Junction, NJ (US);
Yinxiao Liu, Iowa City, IA (US);
Matthias John, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 360 days.

(21) Appl. No.: 13/534,675

(22) Filed: Jun. 27, 2012

(65) Prior Publication Data
US 2013/0057569 A1 Mar. 7, 2013

Related U.S. Application Data

(60) Provisional application No. 61/531,722, filed on Sep. 7, 2011.

(51) Int. Cl.
| | |
|---|---|
| G09G 5/02 | (2006.01) |
| G06T 3/00 | (2006.01) |
| G06K 9/34 | (2006.01) |
| G06K 9/62 | (2006.01) |
| A61B 6/12 | (2006.01) |
| A61B 6/00 | (2006.01) |
| G06T 5/50 | (2006.01) |

(52) U.S. Cl.
CPC ........... *G06T 3/0068* (2013.01); *G06K 9/34* (2013.01); *G06K 9/6289* (2013.01); *G06K 9/6215* (2013.01); *A61B 6/12* (2013.01); *A61B 6/463* (2013.01); *A61B 6/481* (2013.01); *A61B 6/487* (2013.01); *A61B 6/503* (2013.01); *A61B 6/504* (2013.01); *A61B 6/5235* (2013.01); *G06T 5/50* (2013.01); *G06T 2207/10121* (2013.01); *G06T 2207/20076* (2013.01); *G06T 2207/30048* (2013.01); *G06T 2207/30104* (2013.01)

(58) Field of Classification Search
None
See application file for complete search history.

(56) References Cited

U.S. PATENT DOCUMENTS

| | | | | |
|---|---|---|---|---|
| 8,731,271 | B2* | 5/2014 | Van Rens et al. | 382/131 |
| 2006/0257006 | A1* | 11/2006 | Bredno et al. | 382/128 |
| 2009/0192385 | A1* | 7/2009 | Meissner et al. | 600/426 |
| 2010/0290693 | A1* | 11/2010 | Cohen et al. | 382/134 |
| 2011/0182492 | A1* | 7/2011 | Grass et al. | 382/131 |
| 2011/0235889 | A1* | 9/2011 | Spahn | 382/132 |

OTHER PUBLICATIONS

M. Freiman, O. Eliassaf, Y. Taieb, L. Joskowicz, Y. Azraq, J. Sosna; "An iterative Bayesian approach for nearly automatic liver segmentation: algorithm and validation" in International Journal of Computer Assisted Radiology and Surgery Nov. 2008, vol. 3, Issue 5, pp. 439-446.*

* cited by examiner

*Primary Examiner* — James A Thompson
*Assistant Examiner* — Xilin Guo (57) ABSTRACT

A method for fusing 2D fluoroscopic images with 2D angiographic images for real-time interventional procedure guidance includes using a 2-dimensional angiographic image to detect injection of a contrast agent into an anatomical structure, where the contrast agent first appears in a detected image frame, subtracting a background image from the detected image frame and binarizing the subtracted image frame to segment the anatomical structure from the subtracted image frame, registering the segmented anatomical structure with a predefined shape model of the anatomical structure to generate an anatomical mask, generating an anatomical probability map from the anatomical mask using intensity information from the subtracted image frame, where the anatomical probability map expresses a probability of a pixel in the subtracted image frame belonging to the anatomical structure, and fusing the angiographic image with one or more subsequently acquired 2-dimensional fluoroscopic images of the anatomical structure using the anatomical probability map.

18 Claims, 4 Drawing Sheets

2D-2D FUSION FOR INTERVENTIONAL GUIDANCE IN TRANS-CATHETER AORTIC VALVE IMPLANTATION

CROSS REFERENCE TO RELATED UNITED STATES APPLICATIONS

This application claims priority from "2D2D Fusion for Interventional Guidance in TAVI Based on Contrast Detection and Aortic Root Localization", U.S. Provisional Application No. 61/531,722 of Liao, et al., filed Sep. 7, 2011, the contents of which are herein incorporated by reference in their entirety.

TECHNICAL FIELD

This disclosure is directed to methods for visualizing target anatomy for real-time guidance of medical procedures.

DISCUSSION OF THE RELATED ART

Aortic valve disease affect about 1.8% of the global population, and is the most frequent heart valve disease in developed countries, leading to 60,000 surgical aortic valve replacements every year in Europe and even more in the United States. Trans-catheter aortic valve implantation (TAVI) is a new and breakthrough minimally invasive alternative to open heart surgery in patients with severe aortic stenosis. Two dimensional (2D) fluoroscopy is the typical imaging modality for guiding TAVI procedures, where a contrast agent is administered from time to time to show the target anatomy, i.e. the aortic root. During trans-apical TAVI, an antegrade access is used in which a catheter and prosthesis are inserted via small incisions in the chest and the apex of the heart. During trans-femoral TAVI, the catheter is inserted retrogradely via the femoral artery and the aortic arch. Both approaches require X-ray angiographic and fluoroscopic imaging to guide the procedure.

Although recent advances in utilizing three dimensional (3D) models to provide anatomical details further facilitate TAVI, 3D models may not always be available in all TAVI cases. In addition, accurate registration of the 3D model to the 2D fluoroscopy presents a challenge. Hence, a 2D-2D fusion based on the 2D fluoroscopy with occasional contrast administration can facilitate navigation and guidance during TAVI procedures with minimal contrast injection.

SUMMARY

Exemplary embodiments of the invention as described herein generally include methods and systems for 2D-2D fusion of a fluoroscopic frame without contrast injection with an angiographic frame showing the aortic root during TAVI procedures.

According to an aspect of the invention, there is provided a method for fusing 2D fluoroscopic images with 2D angiographic images for real-time interventional procedure guidance, including using a 2-dimensional angiographic image to detect injection of a contrast agent into an anatomical structure, where the contrast agent first appears in a detected image frame, subtracting a background image from the detected image frame and binarizing the subtracted image frame to segment the anatomical structure from the subtracted image frame, registering the segmented anatomical structure with a predefined shape model of the anatomical structure to generate an anatomical mask, generating an anatomical probability map from the anatomical mask using intensity information from the subtracted image frame, where the anatomical probability map expresses a probability of a pixel in the subtracted image frame belonging to the anatomical structure, and fusing the angiographic image with one or more subsequently acquired 2-dimensional fluoroscopic images of the anatomical structure using the anatomical probability map.

According to a further aspect of the invention, binarizing the subtracted image frame comprises inverting the subtracted image frame grayscale, selecting those pixels with an intensity above a lower intensity threshold that are connected to at least one pixel with an intensity above a higher intensity threshold, and performing connected component analysis to remove small isolated regions.

According to a further aspect of the invention, registering the segmented anatomical structure with a predefined shape model of the anatomical structure comprising finding rigid registration parameters $\hat{t}$ that maximize a similarity measure $$\left( \frac{1}{N_{in}} \sum_{p \in SM} I_a(p) - \frac{1}{N_{out}} \sum_{p \notin SM} I_a(p) \right),$$

where SM denotes the predefined shape model of the anatomical structure, $I_a$ denotes the binarized image containing the segmented anatomical structure, and p is a pixel in the binarized image, and applying the rigid registration parameters to the predefined shape model to generate the anatomical mask.

According to a further aspect of the invention, the method includes resealing the predefined shape model of the anatomical structure according to a ratio of a foreground area of the binarized image to an area of the predefined shape model, before maximizing the similarity measure.

According to a further aspect of the invention, the rigid registration parameters $\hat{t}$ include two translations and one rotation.

According to a further aspect of the invention, generating an anatomical probability map includes calculating a first probability $P_d(p)$ of a pixel being within the anatomical structure from $$P_d(p) = \left( \arctan\left( \frac{d(p) - d_{max}/2}{d_{max}/2} \right) + \frac{\pi}{2} \right) / \pi,$$

where d(p) denotes a distance from pixel p to a center of the anatomical mask, and $d_{max}$ is a maximum distance, calculating a second probability $P_i(p)$ of the pixel being within the anatomical structure from $$P_i(p) = \left( \arctan\left( \frac{g_c(p) - t_{low}}{t_{high} - t_{low}} \right) + \frac{\pi}{2} \right) / \pi,$$

where $g_c(p)$ denotes an intensity of pixel p in the inverted subtracted image, $t_{high}$ denotes a higher intensity threshold of the inverted subtracted image intensity histogram, and $t_{low}$ denotes a lower intensity threshold of the inverted subtracted image intensity histogram, and calculating the anatomical probability map from an average of the first probability $P_d(p)$ and the second probability $P_i(p)$.

According to a further aspect of the invention, fusing the angiographic image with a 2-dimensional fluoroscopic image comprises calculating $g(p) = g_c(p) \times P(p) + g_n(p) \times (1 - P(p))$, where P(p) denotes the anatomical probability map at pixel p, g(p) denotes the intensity of pixel p in the fused image, $g_c(p)$ denotes the intensity value of the angiographic image frame at pixel p, and $g_n(p)$ is the intensity value of the fluoroscopic image frame at pixel p.

According to a further aspect of the invention, the anatomical structure is an aortic root.

According to another aspect of the invention, there is provided a method for fusing 2D fluoroscopic images with 2D angiographic images for real-time interventional procedure guidance, including registering an anatomical structure segmented from an angiography image with a predefined shape model of the anatomical structure to generate an anatomical mask, calculating a first probability $P_d(p)$ of a pixel being within the anatomical structure from $$P_d(p) = \left( \arctan\left( \frac{d(p) - d_{max}/2}{d_{max}/2} \right) + \frac{\pi}{2} \right) / \pi,$$

where d(p) denotes a distance from pixel p to a center of the anatomical mask, and $d_{max}$ is a maximum distance, calculating a second probability $P_i(p)$ of the pixel being within the anatomical structure from $$P_i(p) = \left( \arctan\left( \frac{g_c(p) - t_{low}}{t_{high} - t_{low}} \right) + \frac{\pi}{2} \right) / \pi,$$

where $g_c(p)$ denotes an intensity of pixel p in the angiography image, $t_{high}$ denotes a higher intensity threshold of the angiography image intensity histogram, and $t_{low}$ denotes a lower intensity threshold of the angiography image intensity histogram, calculating an anatomical probability map from an average of the first probability $P_d(p)$ and the second probability $P_i(p)$, where the anatomical probability map expresses a probability of a pixel in the subtracted image frame belonging to the anatomical structure, and fusing the angiographic image with one or more subsequently acquired 2-dimensional fluoroscopic images of the anatomical structure using the anatomical probability map.

According to a further aspect of the invention, before registering the segmented anatomical structure with the predefined shape model of the anatomical structure, the method includes using a 2-dimensional image to detect injection of a contrast agent into the anatomical structure, where the contrast agent first appears in a detected image frame, subtracting a background image from the detected image frame and inverting the grayscale of the subtracted detected image to generate the angiography image, and binarizing the inverted subtracted image frame to segment the anatomical structure from angiography image.

According to a further aspect of the invention, binarizing the angiography image selecting those pixels with an intensity above a lower intensity threshold that are connected to at least one pixel with an intensity above a higher intensity threshold, and performing connected component analysis to remove small isolated regions.

According to a further aspect of the invention, fusing the angiographic image with a 2-dimensional fluoroscopic image comprises calculating $g(p) = g_c(p) \times P(p) + g_n(p) \times (1 - P(p))$, where P(p) denotes the anatomical probability map at pixel p, g(p) denotes the intensity of pixel p in the fused image, $g_c(p)$ denotes the intensity value of the angiographic image frame at pixel p, and g(p) is the intensity value of the fluoroscopic image frame at pixel p.

According to another aspect of the invention, there is provided a non-transitory program storage device readable by a computer, tangibly embodying a program of instructions executed by the computer to perform the method steps for fusing 2D fluoroscopic images with 2D angiographic images for real-time interventional procedure guidance.

DETAILED DESCRIPTION OF EXEMPLARY EMBODIMENTS

Exemplary embodiments of the invention as described herein generally include systems and methods for 2D-2D fusion of a fluoroscopic frame without contrast injection with an angiographic frame showing the aortic root during TAVI procedures. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A method according to an embodiment of the invention for 2D-2D fusion of a fluoroscopic frame without contrast injection and an angiographic frame with contrast injection can show the aortic root during a TAVI procedure. In particular, for an online X-ray image stream, the event of contrast injection into the aortic root can be automatically detected, and the location of the aortic root can be estimated from the detected contrasted frame. An aorta probability map (APM) is then calculated from the contrasted frame and used to generate the fusion of the contrasted angiography and the non-contrasted fluoroscopic frames for visualization purpose.

Figure 1:
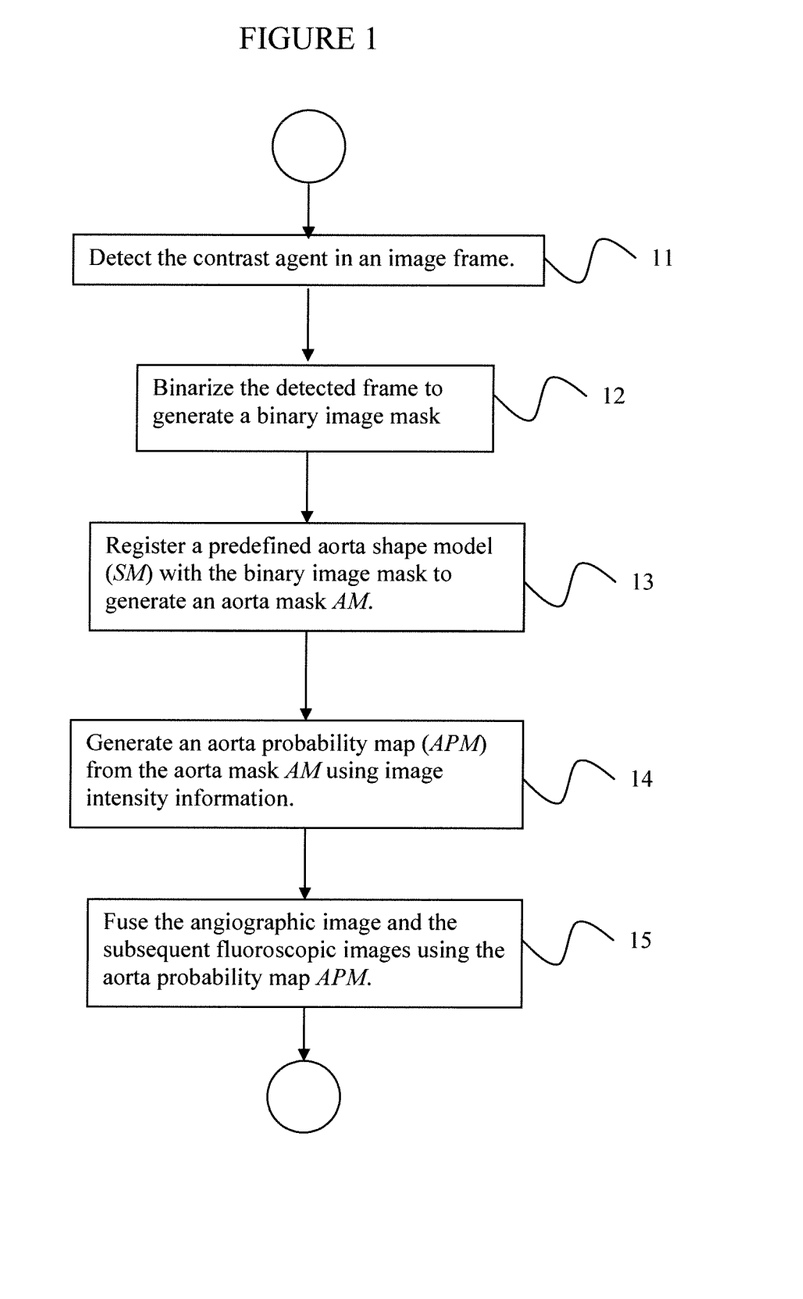
FIG. 1 is a flowchart of a method for 2D-2D fusion of a fluoroscopic frame with an angiographic frame without contrast injection, according to an embodiment of the invention.

FIG. 1 is a flowchart of a method for 2D-2D fusion of a fluoroscopic frame without contrast injection and an angiographic frame with contrast injection, according to an embodiment of the invention. Referring now to the figure, a procedure begins at step 11 by detecting contrast. For an online X-ray image stream, an image-based event detector is deployed to detect the injection of a contrast agent into the aortic root. Once the contrast agent is detected in a frame, steps 12 to 15 may be performed. Note that in the following data acquisitions there is no contrast injection, and there is no need to detect the aortic root there. Embodiments of the invention assume there is no relative motion between the contrasted frame and the non-contrasted frame other than cardiac/respiratory motion, which is estimated by the surrogated signal, such as the movement of the pigtail catheter or the calcium close to the aortic root.

Figure 2:
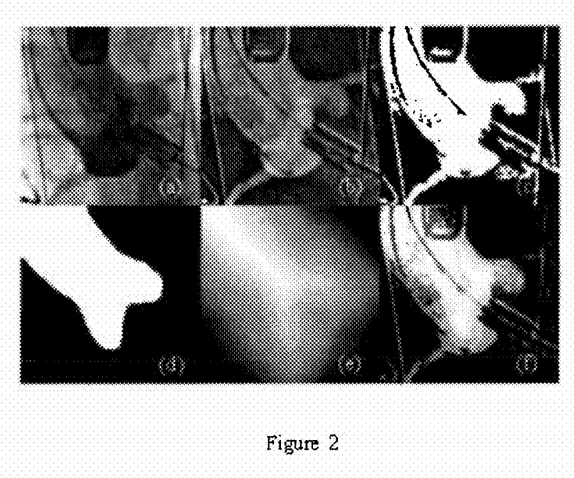
FIGS. 2(a)-(f) illustrate various stages of a method according to an embodiment of the invention.

At step 12, binarization is performed. A background image is subtracted from the detected frame with the most contrast injection, to generate a subtracted angiography image which is then inverted to depict a bright aorta root shape. FIG. 2(*a*) depicts an ROI around the aorta in the contrasted frame. FIG. 2(*b*) shows the result of subtracting a background image from the image of FIG. 2(*a*) after inversion, resulting in an image with bright aorta root shape. Next, hysteresis thresholding with two thresholds is performed on a grayscale histogram of the inverted subtracted image. An exemplary, non-limiting the lower threshold is at the 60th percentile of the total histogram, and an exemplary, non-limiting higher threshold is at the 90th percentile. Note that different higher and lower thresholds can be used in other embodiments of the invention. All pixels with an intensity value higher than the lower threshold and also connected to at least some pixels above the higher threshold are segmented. In some embodiments, connected component analysis can then be performed to remove small isolated regions. FIG. 2(*c*) illustrates a binary aortic image mask generated after hysteresis thresholding and connectivity analysis.

Next, at step 13, registration between a predefined aorta shape model (SM) and the binarized aortic image obtained in step 12 is performed to locate the aortic root. The predefined SM is first rescaled according to a ratio of the area of the foreground of the binarized image with respect to the SM. Note that the SM has units defined in terms of pixels. According to an embodiment of the invention, the SM is then rigidly registered by estimating three parameters, two translational and one rotational, using the following similarity measure:

$$\hat{t} = \max_t \left( \frac{1}{N_{in}} \sum_{p \in SM} I_a(p) - \frac{1}{N_{out}} \sum_{p \notin SM} I_a(p) \right), \quad (1)$$

where $I_a$ is the binary image and p is a pixel in that image, $\hat{t}$ is the three parameters of translations and rotation to be estimated, and $N_{in}$ and $N_{out}$ are the respective number of pixels inside and outside of the boundary of the registered shape model SM. The parameter vector $\hat{t}$ does not appear explicitly in EQ. (1) but rather affects the overlap of the aorta shape model SM and the binarized foreground, and hence the number of pixels inside and outside the boundary of the aorta shape model. Applying the registration parameters to the predefined aorta shape model (SM) results in an aorta mask AM, as shown in FIG. 2(*d*).

An aorta probability map (APM) is generated at step 14. The APM can be generated utilizing information from both the image intensity and the aorta mask. In particular, a distance transform is calculated on the AM generated in step 13 to provide a smooth representation of the aorta. The value in the distance transform indicates how close a pixel is to the center of AM, as shown in FIG. 2(*e*). If a pixel is deep inside the mask, the probability that it belongs to the aorta will be high. Conversely, if a pixel is far away from the mask, the probability that it belongs to the aorta will be low. An aorta probability for pixel p from the SM can be defined as:

$$P_d(p) = \left( \arctan\left( \frac{d(p) - d_{max}/2}{d_{max}/2} \right) + \frac{\pi}{2} \right) \bigg/ \pi, \quad (2)$$

where d(p) denotes the distance value at pixel p, and $d_{max}$ denotes the maximum value of the distance transform. By utilizing information from the AM, as expressed by EQ. (2), above, some nonhomogenous regions inside the aorta shape caused by, for example, the ultrasound probe, can be filled, and some non-aortic structures outside the aorta such as the wires can be removed.

In addition, if a pixel has a high intensity value in the subtracted image, the probability that it belongs to the aorta will be high, and if a pixel has a low intensity value in the subtracted image, the probability that it belongs to the aorta will be low. The aorta probability for pixel p from the intensity can be defined as:

$$P_i(p) = \left( \arctan\left( \frac{g_c(p) - t_{low}}{t_{high} - t_{low}} \right) + \frac{\pi}{2} \right) \bigg/ \pi, \quad (3)$$

where $g_c(p)$ denotes the intensity of pixel p in the inverted subtracted image, $t_{high}$ denotes the intensity of the higher threshold of the inverted subtracted image intensity histogram, and $t_{low}$ denotes the intensity of the lower threshold of the intensity histogram.

The final APM P(p) for pixel p can be defined as the following average:

$$P(p) = \tfrac{1}{2}(P_i(p) + P_d(p)). \quad (4)$$

The final aorta probability map (APM), combining both intensity and aorta model information, is shown in FIG. 2(*f*).

At step 15, fusion of fluoroscopy and angiography is performed. The estimated aorta probability map APM is used for the fusion of the aorta onto the subsequent fluoroscopic frames without contrast injection. For a given pixel p, the higher its probability in the aorta map, the darker its intensity on the fused image. In particular, the intensity value g(p) for a given pixel p in the fused image can be calculated as:

$$g(p) = g_c(p) \times P(p) + g_n(p) \times (1 - P(p)), \quad (5)$$

where P(p) is the APM at pixel p, $g_c(p)$ denotes the intensity value of the angiographic frame at pixel p, and $g_n(p)$ is the intensity value of a fluoroscopic frame at pixel p.

When there is motion between the fluoroscopic frame and the aortic angiography (and hence the estimated aorta probability map), the estimated motion parameters need to be applied to the estimated aorta probability map before fusion. The motion between the angiography image and the fluoroscopy images can be automatically estimated by various means, such as tracking of the movement of the "pigtail" or the calcium close to the aortic root.

Figure 3:
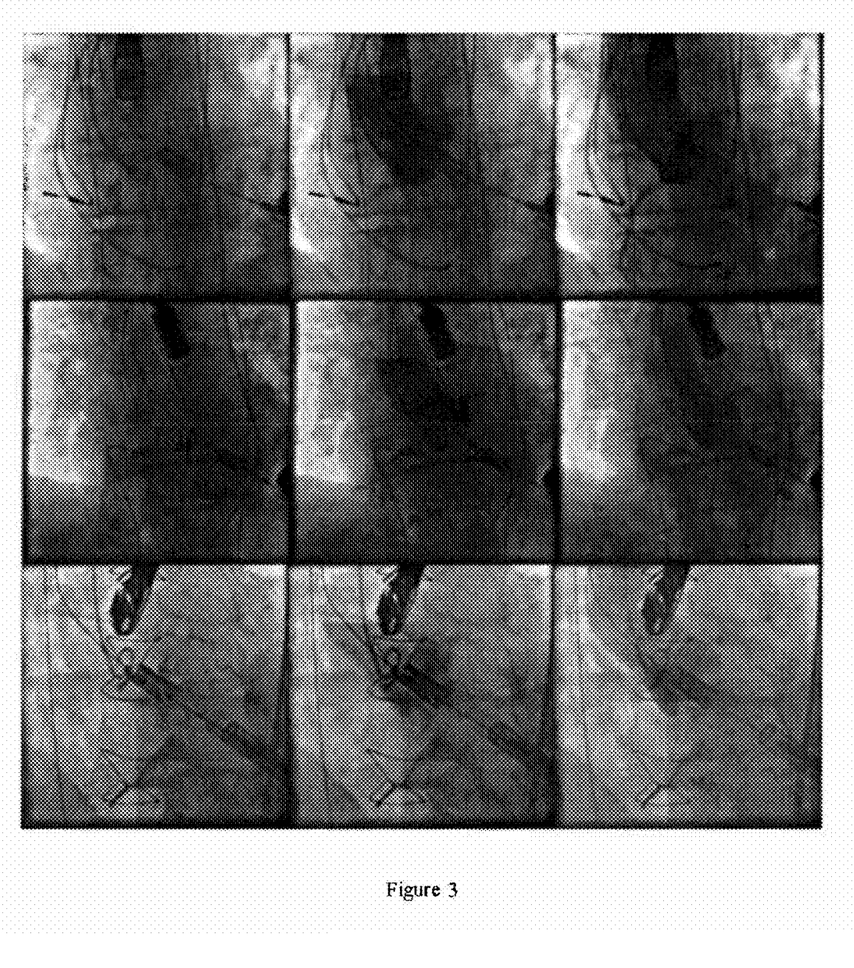
FIG. 3 illustrates 3 examples of 2D-2D fusion results, according to embodiments of the invention.

FIG. 3 illustrates three examples of 2D-2D fusion results, each row representing one patient case. The left column depicts the original non-contrasted frames; the center column depicts the 2D-2D fusion results; and the right column depicts contrasted frames from which the aorta probability map is calculated.

A 2D-2D fusion method according to an embodiment of the invention is not limited to a TAVI procedure and can be applied to other interventional procedures requiring overlay of an angiographic image showing the target organ with the real-time fluoroscopic images monitoring the procedures, as will be understood by those of skill in the art.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 4:
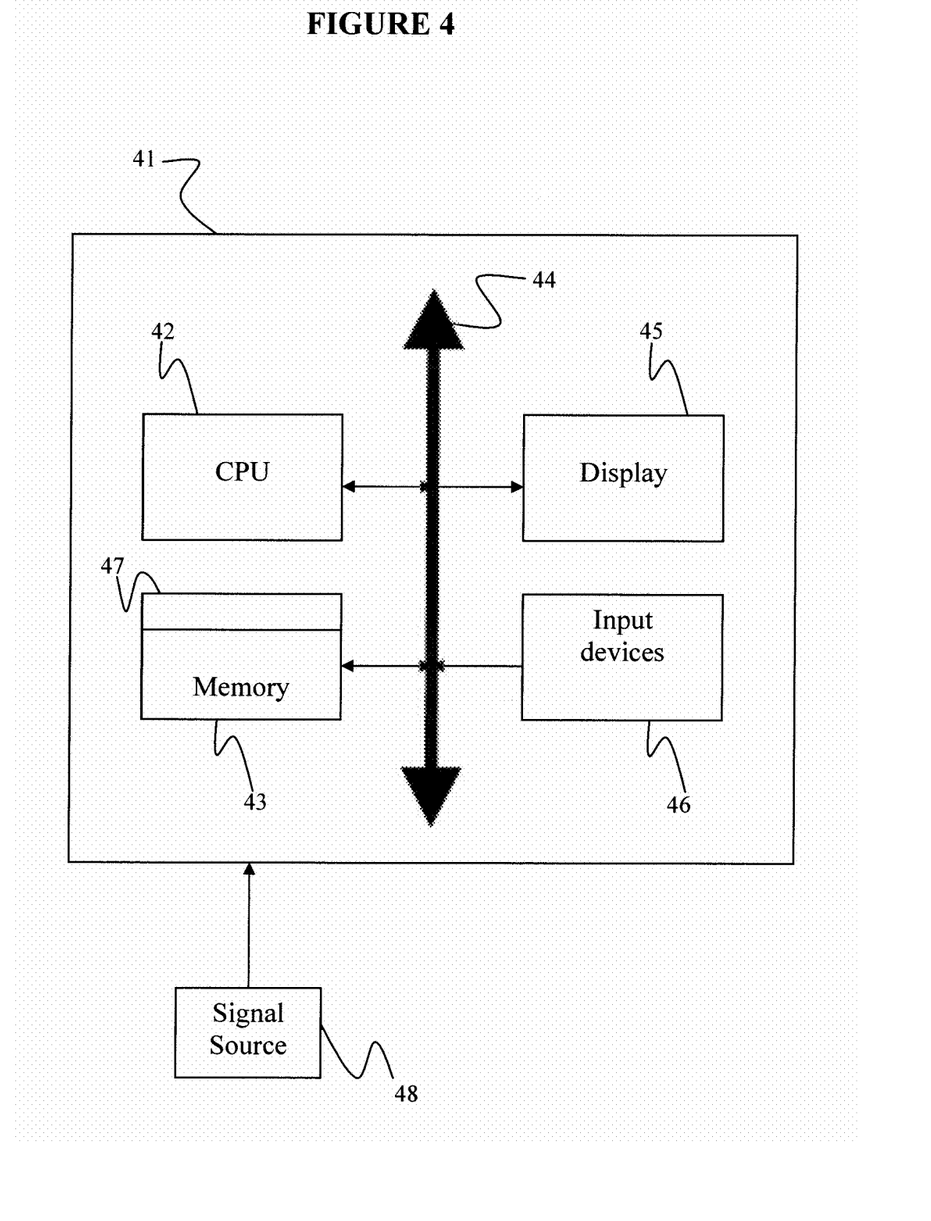
FIG. 4 is a block diagram of an exemplary computer system for implementing a method for 2D-2D fusion of a fluoroscopic frame without contrast injection with an angiographic frame, according to an embodiment of the invention.

FIG. 4 is a block diagram of an exemplary computer system for implementing a method for 2D-2D fusion of a fluoroscopic frame without contrast injection with an angiographic frame according to an embodiment of the invention. Referring now to FIG. 4, a computer system 41 for implementing the present invention can comprise, hater alia, a central processing unit (CPU) 42, a memory 43 and an input/output (I/O) interface 44. The computer system 41 is generally coupled through the I/O interface 44 to a display 45 and various input devices 46 such as a mouse and a keyboard. The support circuits can include circuits such as cache, power supplies, clock circuits, and a communication bus. The memory 43 can include random access memory (RAM), read only memory (ROM), disk drive, tape drive, etc., or a combinations thereof. The present invention can be implemented as a routine 47 that is stored in memory 43 and executed by the CPU 42 to process the signal from the signal source 48. As such, the computer system 41 is a general purpose computer system that becomes a specific purpose computer system when executing the routine 47 of the present invention.

The computer system 41 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for fusing 2D fluoroscopic images with 2D angiographic images for real-time interventional procedure guidance, said method comprising the steps of:

using a 2-dimensional angiographic image to detect injection of a contrast agent into an anatomical structure, wherein the contrast agent first appears in a detected image frame;

subtracting a background image from the detected image frame and binarizing the subtracted image frame to segment the anatomical structure from the subtracted image frame;

registering the segmented anatomical structure with a predefined shape model of the anatomical structure to generate an anatomical mask;

generating an anatomical probability map from the anatomical mask using intensity information from the subtracted image frame, wherein the anatomical probability map expresses a probability of a pixel in the subtracted image frame belonging to the anatomical structure; and fusing the angiographic image with one or more subsequently acquired 2-dimensional fluoroscopic images of the anatomical structure using the anatomical probability map to generate a fused image of the anatomical structure by calculating $g(p)=g_c(p) \times P(p) + g_n(p) \times (1-P(p))$, where $P(p)$ denotes the anatomical probability map at pixel p, $g(p)$ denotes the intensity of pixel p in the fused image, $g_c(p)$ denotes the intensity value of the angiographic image frame at pixel p, and $g_n(p)$ is the intensity value of the fluoroscopic image frame at pixel p, wherein the steps of using a 2-dimensional angiographic image to detect injection of a contrast agent, subtracting a background image, registering the segmented anatomical structure, generating an anatomical probability map, and fusing the angiographic image are performed by a computer.

2. The method of claim 1, wherein binarizing the subtracted image frame comprises inverting the subtracted image frame grayscale, selecting those pixels with an intensity above a lower intensity threshold that are connected to at least one pixel with an intensity above a higher intensity threshold, and performing connected component analysis to remove small isolated regions.

3. The method of claim 1, wherein registering the segmented anatomical structure with a predefined shape model of the anatomical structure comprising finding rigid registration parameters $\hat{t}$ that maximize a similarity measure $$\left( \frac{1}{N_{in}} \sum_{p \in SM} I_a(p) - \frac{1}{N_{out}} \sum_{p \notin SM} I_a(p) \right),$$

wherein SM denotes the predefined shape model of the anatomical structure, $I_a$ denotes the binarized image containing the segmented anatomical structure, and p is a pixel in the binarized image, and applying the rigid registration parameters to the predefined shape model to generate the anatomical mask.

4. The method of claim 3, further comprising rescaling the predefined shape model of the anatomical structure according to a ratio of a foreground area of the binarized image to an area of the predefined shape model, before maximizing the similarity measure.

5. The method of claim 3, wherein the rigid registration parameters $\hat{t}$ include two translations and one rotation.

6. The method of claim 1, wherein generating an anatomical probability map comprises:
calculating a first probability $P_d(p)$ of a pixel being within the anatomical structure from $$P_d(p) = \left(\arctan\left(\frac{d(p) - d_{max}/2}{d_{max}/2}\right) + \frac{\pi}{2}\right)\bigg/\pi,$$

wherein $d(p)$ denotes a distance from pixel p to a center of the anatomical mask, and $d_{max}$ is a maximum distance;
calculating a second probability $P_i(p)$ of the pixel being within the anatomical structure from $$P_i(p) = \left(\arctan\left(\frac{g_c(p) - t_{low}}{t_{high} - t_{low}}\right) + \frac{\pi}{2}\right)\bigg/\pi,$$

wherein $g_c(p)$ denotes an intensity of pixel p in the inverted subtracted image, $t_{high}$ denotes a higher intensity threshold of the inverted subtracted image intensity histogram, and $t_{low}$ denotes a lower intensity threshold of the inverted subtracted image intensity histogram; and
calculating the anatomical probability map from an average of the first probability $P_d(p)$ and the second probability $P_i(p)$.

7. The method of claim 1, wherein the anatomical structure is an aortic root.

8. A method for fusing 2D fluoroscopic images with 2D angiographic images for real-time interventional procedure guidance, said method comprising the steps of:
registering an anatomical structure segmented from an angiography image with a predefined shape model of the anatomical structure to generate an anatomical mask;
calculating a first probability $P_d(p)$ of a pixel being within the anatomical structure from $$P_d(p) = \left(\arctan\left(\frac{d(p) - d_{max}/2}{d_{max}/2}\right) + \frac{\pi}{2}\right)\bigg/\pi,$$

wherein $d(p)$ denotes a distance from pixel p to a center of the anatomical mask, and $d_{max}$ is a maximum distance;
calculating a second probability $P_i(p)$ of the pixel being within the anatomical structure from $$P_i(p) = \left(\arctan\left(\frac{g_c(p) - t_{low}}{t_{high} - t_{low}}\right) + \frac{\pi}{2}\right)\bigg/\pi,$$

wherein $g_c(p)$ denotes an intensity of pixel p in the angiography image, $t_{high}$ denotes a higher intensity threshold of the angiography image intensity histogram, and $t_{low}$ denotes a lower intensity threshold of the angiography image intensity histogram;
calculating an anatomical probability map from an average of the first probability $P_d(p)$ and the second probability $P_i(p)$, wherein the anatomical probability map expresses a probability of a pixel in the subtracted image frame belonging to the anatomical structure; and
fusing the angiographic image with one or more subsequently acquired 2-dimensional fluoroscopic images of the anatomical structure using the anatomical probability map to generate a fused image of the anatomical structure,
wherein the steps of registering an anatomical structure, calculating a first probability, calculating a second probability, calculating an anatomical probability map, and fusing the angiographic image are performed by a computer.

9. The method of claim 8, further comprising, before registering the segmented anatomical structure with the predefined shape model of the anatomical structure:
using a 2-dimensional image to detect injection of a contrast agent into the anatomical structure, wherein the contrast agent first appears in a detected image frame;
subtracting a background image from the detected image frame and inverting the grayscale of the subtracted detected image to generate the angiography image; and
binarizing the inverted subtracted image frame to segment the anatomical structure from angiography image.

10. The method of claim 8, wherein binarizing the angiography image selecting those pixels with an intensity above a lower intensity threshold that are connected to at least one pixel with an intensity above a higher intensity threshold, and performing connected component analysis to remove small isolated regions.

11. The method of claim 8, wherein fusing the angiographic image with a 2-dimensional fluoroscopic image comprises calculating
$g(p)=g_c(p)\times P(p)+g_n(p)\times(1-P(p))$, where $P(p)$ denotes the anatomical probability map at pixel p, $g(p)$ denotes the intensity of pixel p in the fused image, $g_c(p)$ denotes the intensity value of the angiographic image frame at pixel p, and $g_n(p)$ is the intensity value of the fluoroscopic image frame at pixel p.

12. A non-transitory program storage device readable by a computer, tangibly embodying a program of instructions executed by the computer to perform the method steps for fusing 2D fluoroscopic images with 2D angiographic images for real-time interventional procedure guidance, said method comprising the steps of:
using a 2-dimensional angiographic image to detect injection of a contrast agent into an anatomical structure, wherein the contrast agent first appears in a detected image frame;
subtracting a background image from the detected image frame and binarizing the subtracted image frame to segment the anatomical structure from the subtracted image frame;
registering the segmented anatomical structure with a predefined shape model of the anatomical structure to generate an anatomical mask by finding rigid registration parameters $\hat{t}$ that maximize a similarity measure $$\left(\frac{1}{N_{in}}\sum_{p\in SM} I_a(p) - \frac{1}{N_{out}}\sum_{p\notin SM} I_a(p)\right),$$

wherein SM denotes the predefined shape model of the anatomical structure, $I_a$ denotes the binarized image containing the segmented anatomical structure, and p is a pixel in the binarized image, and applying the rigid registration parameters to the predefined shape model to generate the anatomical mask;
generating an anatomical probability map from the anatomical mask using intensity information from the subtracted image frame, wherein the anatomical probability map expresses a probability of a pixel in the subtracted image frame belonging to the anatomical structure; and fusing the angiographic image with one or more subsequently acquired 2-dimensional fluoroscopic images of the anatomical structure using the anatomical probability map to generate a fused image of the anatomical structure.

13. The computer readable program storage device of claim 12, wherein binarizing the subtracted image frame comprises inverting the subtracted image frame grayscale, selecting those pixels with an intensity above a lower intensity threshold that are connected to at least one pixel with an intensity above a higher intensity threshold, and performing connected component analysis to remove small isolated regions.

14. The computer readable program storage device of claim 12, the method further comprising rescaling the predefined shape model of the anatomical structure according to a ratio of a foreground area of the binarized image to an area of the predefined shape model, before maximizing the similarity measure.

15. The computer readable program storage device of claim 12, wherein the rigid registration parameters $\hat{t}$ include two translations and one rotation.

16. The computer readable program storage device of claim 12, wherein generating an anatomical probability map comprises:
calculating a first probability $P_d(p)$ of a pixel being within the anatomical structure from $$P_d(p) = \left(\arctan\left(\frac{d(p) - d_{max}/2}{d_{max}/2}\right) + \frac{\pi}{2}\right)/\pi,$$

wherein $d(p)$ denotes a distance from pixel p to a center of the anatomical mask, and $d_{max}$ is a maximum distance;

calculating a second probability $P_i(p)$ of the pixel being within the anatomical structure from $$P_i(p) = \left(\arctan\left(\frac{g_c(p) - t_{low}}{t_{high} - t_{low}}\right) + \frac{\pi}{2}\right)/\pi,$$

wherein $g_c(p)$ denotes an intensity of pixel p in the inverted subtracted image, $t_{high}$ denotes a higher intensity threshold of the inverted subtracted image intensity histogram, and $t_{low}$ denotes a lower intensity threshold of the inverted subtracted image intensity histogram; and calculating the anatomical probability map from an average of the first probability $P_d(p)$ and the second probability $P_i(p)$.

17. The computer readable program storage device of claim 12, wherein fusing the angiographic image with a 2-dimensional fluoroscopic image comprises calculating $g(p) = g_c(p) \times P(p) + g_n(p) \times (1 - P(p))$, where $P(p)$ denotes the anatomical probability map at pixel p, $g(p)$ denotes the intensity of pixel p in the fused image, $g_c(p)$ denotes the intensity value of the angiographic image frame at pixel p, and $g_n(p)$ is the intensity value of the fluoroscopic image frame at pixel p.

18. The computer readable program storage device of claim 12, wherein the anatomical structure is an aortic root.

* * * * *